US010130806B2

(12) United States Patent
Leven et al.

(10) Patent No.: US 10,130,806 B2
(45) Date of Patent: Nov. 20, 2018

(54) SYSTEMS AND METHODS FOR MAKING AND USING A TEMPORARY LEAD

(71) Applicant: Boston Scientific Neuromodulation Corporation, Valencia, CA (US)

(72) Inventors: Jacob B. Leven, Huntington Beach, CA (US); John M. Barker, Ventura, CA (US); Anne Margaret Pianca, Santa Monica, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 235 days.

(21) Appl. No.: 15/192,908

(22) Filed: Jun. 24, 2016

(65) Prior Publication Data

US 2016/0375238 A1    Dec. 29, 2016

Related U.S. Application Data

(60) Provisional application No. 62/185,432, filed on Jun. 26, 2015.

(51) Int. Cl.
*A61N 1/05* (2006.01)
*A61N 1/375* (2006.01)
*A61N 1/36* (2006.01)
*A61N 1/372* (2006.01)

(52) U.S. Cl.
CPC ......... *A61N 1/0551* (2013.01); *A61N 1/0553* (2013.01); *A61N 1/3752* (2013.01); *A61N 1/3605* (2013.01); *A61N 1/37241* (2013.01)

(58) Field of Classification Search
CPC ...... A61N 1/3752; A61N 1/05; A61N 1/0551; A61N 1/053; A61N 1/0553
See application file for complete search history.

(56) References Cited

U.S. PATENT DOCUMENTS

| | | | | |
|---|---|---|---|---|
| 4,572,605 A * | 2/1986 | Hess | ...... | H01R 24/58 |
| | | | | 439/585 |
| 5,007,435 A * | 4/1991 | Doan | ...... | A61N 1/056 |
| | | | | 607/119 |
| 5,354,326 A * | 10/1994 | Comben | ...... | H01R 24/58 |
| | | | | 439/299 |
| 5,782,892 A | 7/1998 | Castle et al. | | |
| 5,931,861 A * | 8/1999 | Werner | ...... | A61N 1/3752 |
| | | | | 607/115 |
| 6,038,479 A | 3/2000 | Werner et al. | | |

(Continued)

FOREIGN PATENT DOCUMENTS

EP    2535009    12/2012
WO   2012/075497    6/2012

*Primary Examiner* — George Evanisko
(74) *Attorney, Agent, or Firm* — Lowe Graham Jones PLLC; Bruce E. Black (57) ABSTRACT

A trial electrical stimulation lead includes a lead body having a distal end portion, a proximal end portion, and a longitudinal length; electrodes disposed along the distal end portion of the lead body; terminals disposed along the proximal end portion of the lead body; conductors electrically coupling the terminals to the electrodes; and a preventer extending proximally from the proximal end portion of the lead body. The preventer has a diameter smaller than a diameter of the lead body. The preventer prevents coupling of the trial electrical stimulation lead to an implantable control module, but permits coupling to an external trial stimulation system.

16 Claims, 10 Drawing Sheets

(56) References Cited

U.S. PATENT DOCUMENTS

| | | | |
|---|---|---|---|
| 6,038,481 A | 3/2000 | Werner et al. | |
| 6,181,969 B1 | 1/2001 | Gord | |
| 6,192,278 B1 | 2/2001 | Werner et al. | |
| 6,343,233 B1 | 1/2002 | Werner et al. | |
| 6,397,108 B1 | 5/2002 | Camps et al. | |
| 6,516,227 B1 | 2/2003 | Meadows et al. | |
| 6,609,029 B1 | 8/2003 | Mann et al. | |
| 6,609,032 B1 | 8/2003 | Woods et al. | |
| 6,687,538 B1 | 2/2004 | Hrdlicka et al. | |
| 6,741,892 B1 * | 5/2004 | Meadows | A61N 1/3752 607/116 |
| 6,950,709 B2 | 9/2005 | Baudino | |
| 6,980,863 B2 * | 12/2005 | van Venrooij | A61N 1/0529 607/116 |
| 7,130,699 B2 * | 10/2006 | Huff | A61N 1/05 607/116 |
| 7,244,150 B1 | 7/2007 | Brase et al. | |
| 7,437,193 B2 | 10/2008 | Parramon et al. | |
| 7,493,159 B2 | 2/2009 | Hrdlicka et al. | |
| 7,539,542 B1 | 5/2009 | Malinowski | |
| 7,548,788 B2 | 6/2009 | Chinn et al. | |
| 7,563,141 B2 | 7/2009 | Alexander et al. | |
| 7,594,828 B2 | 9/2009 | Alexander et al. | |
| 7,633,023 B1 | 12/2009 | Cappa et al. | |
| 7,672,734 B2 | 3/2010 | Anderson et al. | |
| 7,736,192 B2 | 6/2010 | Alexander et al. | |
| 7,761,165 B1 | 7/2010 | He et al. | |
| 7,949,395 B2 | 5/2011 | Kuzma | |
| 7,974,706 B2 | 7/2011 | Moffitt et al. | |
| 8,175,710 B2 | 5/2012 | He | |
| 8,224,450 B2 | 7/2012 | Brase | |
| 8,239,042 B2 | 8/2012 | Chinnn et al. | |
| 8,364,278 B2 | 1/2013 | Pianca et al. | |
| 8,401,670 B2 | 3/2013 | Mehdizadeh et al. | |
| 8,849,396 B2 | 9/2014 | DeRohan et al. | |
| 9,101,775 B2 | 8/2015 | Barker | |
| 2003/0199948 A1 | 10/2003 | Kokones et al. | |
| 2004/0106964 A1 | 6/2004 | Fischer, Sr. et al. | |
| 2005/0165465 A1 | 7/2005 | Pianca et al. | |
| 2007/0150036 A1 | 6/2007 | Anderson | |
| 2007/0197896 A1 | 8/2007 | Moll et al. | |
| 2010/0070012 A1 | 3/2010 | Chinn et al. | |
| 2010/0106204 A1 | 4/2010 | Moffitt et al. | |
| 2010/0249869 A1 | 9/2010 | Ries et al. | |
| 2011/0098795 A1 | 4/2011 | Mendizadeh et al. | |
| 2011/0218549 A1 | 9/2011 | Barker | |
| 2013/0098678 A1 | 4/2013 | Barker | |
| 2015/0025609 A1 | 1/2015 | Govea | |
| 2016/0166836 A1 | 6/2016 | Shanahan et al. | |
| 2016/0206891 A1 | 7/2016 | Howard et al. | |

* cited by examiner

SYSTEMS AND METHODS FOR MAKING AND USING A TEMPORARY LEAD

CROSS-REFERENCE TO RELATED APPLICATIONS

This application claims the benefit under 35 U.S.C. § 119(e) of U.S. Provisional Patent Application Ser. No. 62/185,432, filed Jun. 26, 2015, which is incorporated herein by reference.

FIELD

The present invention is directed to the area of implantable electrical stimulation systems and methods of making and using the systems. The present invention is also directed to a trial lead and its use with an operating room cable configured and arranged to electrically couple the trial lead to a trial stimulator, as well as methods of making and using the system, operating room cable, and lead.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients. Stimulation of the brain, such as deep brain stimulation, can be used to treat a variety of diseases or disorders.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

One embodiment is a trial electrical stimulation lead including a lead body having a distal end portion, a proximal end portion, and a longitudinal length; electrodes disposed along the distal end portion of the lead body; terminals disposed along the proximal end portion of the lead body; conductors electrically coupling the terminals to the electrodes; and a preventer extending proximally from the proximal end portion of the lead body. The preventer has a diameter smaller than a diameter of the lead body.

In at least some embodiments, the lead body defines a central lumen extending from the proximal end portion to the distal end portion, where a portion of the preventer is disposed within the central lumen. In at least some embodiments, the preventer is a tube defining a lumen extending along the tube. In at least some embodiments, the lumen of the preventer is in communication with the central lumen of the lead body. In at least some embodiments, the lead further includes a stylet configured and arranged for insertion through the lumen of the preventer into the central lumen of the lead body.

In at least some embodiments, the preventer includes a proximal tip that is flared, beveled, or has a radiused inside edge to facilitate insertion of a stylet into the lumen of the preventer. In at least some embodiments, the portion of the preventer disposed within the central lumen is disposed radially beneath at least one of the terminals. In at least some embodiments, the portion of the preventer disposed within the central lumen is disposed radially beneath all of the terminals.

In at least some embodiments, the preventer further includes a polymer jacket disposed over the tube of the preventer to soften an outer surface of the preventer. In at least some embodiments, the polymer jacket includes a proximal tip that is flared, beveled, or has a radiused inside edge.

Another embodiment is an electrical stimulation system including any of the electrical stimulation leads described above and an operating room cable for electrically coupling the electrical stimulation lead to a trial stimulator. The operating room cable includes an elongated body having a first end and an opposing second end; a trial stimulator connector disposed at the first end of the body, and electrically coupleable with the trial stimulator; and a lead connector disposed at the second end of the body and electrically coupled to the trial stimulator connector. The lead connector is configured and arranged to mechanically receive the proximal end portion of the electrical stimulation lead.

In at least some embodiments, the lead connector includes a housing, a first lead aperture in the housing for receiving the proximal end portion of the lead, and a side slit defined along the housing, parallel the first lead aperture, and in communication with the first lead aperture. In at least some embodiments, a width of the side slit is less than a diameter of the lead body of the electrical stimulation lead. In at least some embodiments, the width of the side slit is more than a diameter of the preventer of the electrical stimulation lead.

In at least some embodiments, the electrical stimulation system further includes a control module including a housing, and an electronic subassembly disposed in the housing; and a connector having a proximal end, a distal end, and a longitudinal length, the connector including a connector housing defining a port at the distal end of the connector, and a plurality of connector contacts disposed in the connector housing. In at least some embodiments, the control module includes the connector and the system is configured and arranged so that, when the electrical stimulation lead is inserted into the connector, the terminals of the electrical stimulation lead are prevented from making contact with the connector contacts by the preventer.

In at least some embodiments, the electrical stimulation system further includes a lead extension coupleable to the control module. In at least some embodiments, the lead extension includes the connector, wherein the system is configured and arranged so that, when the electrical stimulation lead is inserted into the connector, the terminals of the electrical stimulation lead are prevented from making contact with the connector contacts by the preventer.

A further embodiment is a method of using any of the electrical stimulation leads described above. The method includes inserting the electrical stimulation lead into a patient and coupling the electrical stimulation lead to a cable of an external trial stimulation system. In at least some embodiments, the method further includes removing the electrical stimulation lead; implanting a permanent electrical stimulation lead into the patient; and coupling the permanent electrical stimulation lead to an implantable control module.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to a trial lead and its use with an operating room cable configured and arranged to electrically couple the trial lead to a trial stimulator, as well as methods of making and using the system, operating room cable, and lead.

Suitable implantable electrical stimulation systems include, but are not limited to, a least one lead with one or more electrodes disposed along a distal end of the lead and one or more terminals disposed along the one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,949,395; 7,244,150; 7,672,734; 7,761,165; 7,974,706; 8,175,710; 8,224,450; and 8,364,278; and U.S. Patent Application Publication No. 2007/0150036, all of which are incorporated by reference in their entirety.

Figure 1:
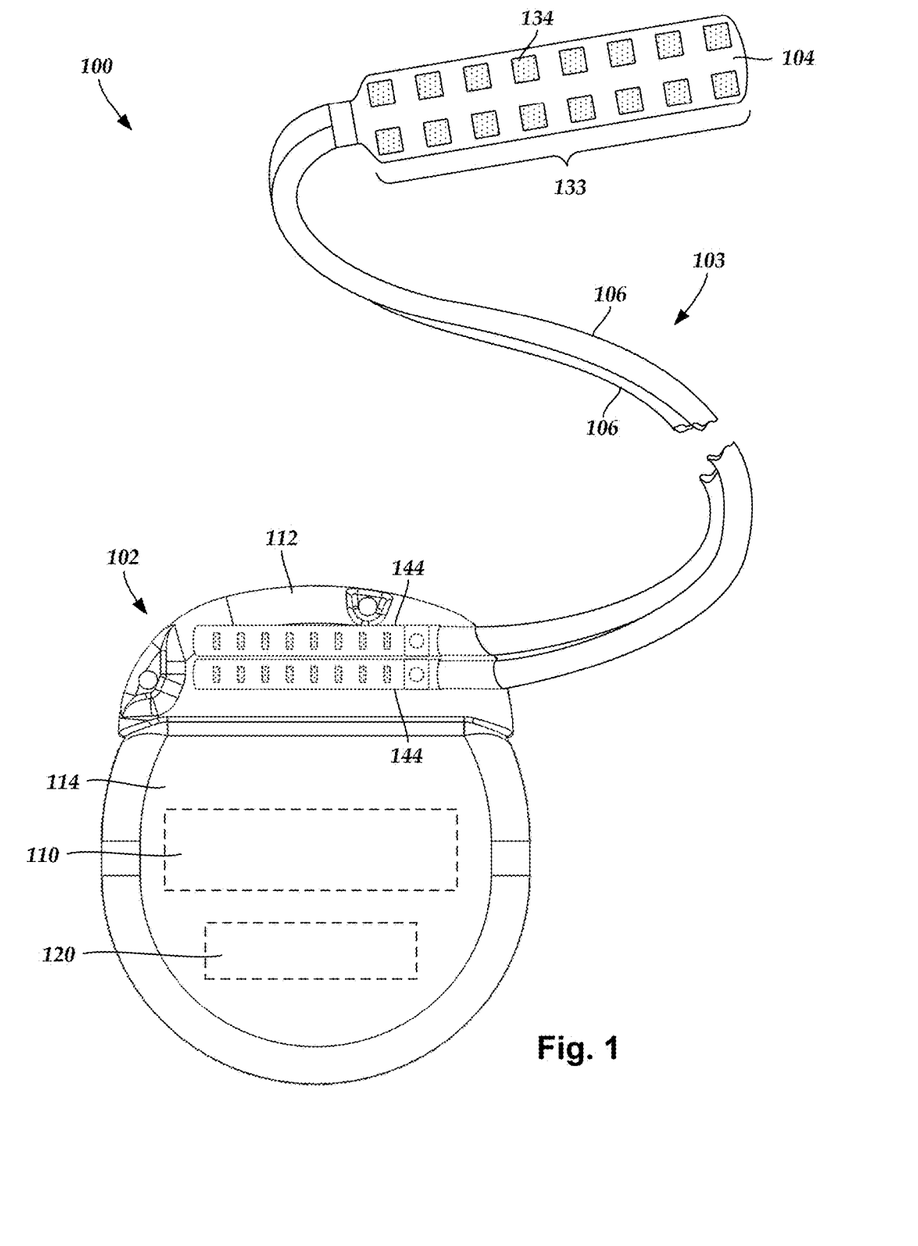
FIG. 1 is a schematic view of one embodiment of an electrical stimulation system that includes a paddle lead electrically coupled to a control module, according to the invention.

FIG. 1 illustrates schematically one embodiment of an electrical stimulation system 100. The electrical stimulation system includes a control module (e.g., a stimulator or pulse generator) 102 and a lead 103 coupleable to the control module 102. The lead 103 includes a paddle body 104 and one or more lead bodies 106. In FIG. 1, the lead 103 is shown having two lead bodies 106. It will be understood that the lead 103 can include any suitable number of lead bodies including, for example, one, two, three, four, five, six, seven, eight or more lead bodies 106. An array 133 of electrodes, such as electrode 134, is disposed on the paddle body 104, and an array of terminals (e.g., 310 in FIG. 3A-3B) is disposed along each of the one or more lead bodies 106.

It will be understood that the electrical stimulation system can include more, fewer, or different components and can have a variety of different configurations including those configurations disclosed in the electrical stimulation system references cited herein. For example, instead of a paddle body, the electrodes can be disposed in an array at or near the distal end of a lead body forming a percutaneous lead.

Figure 2:
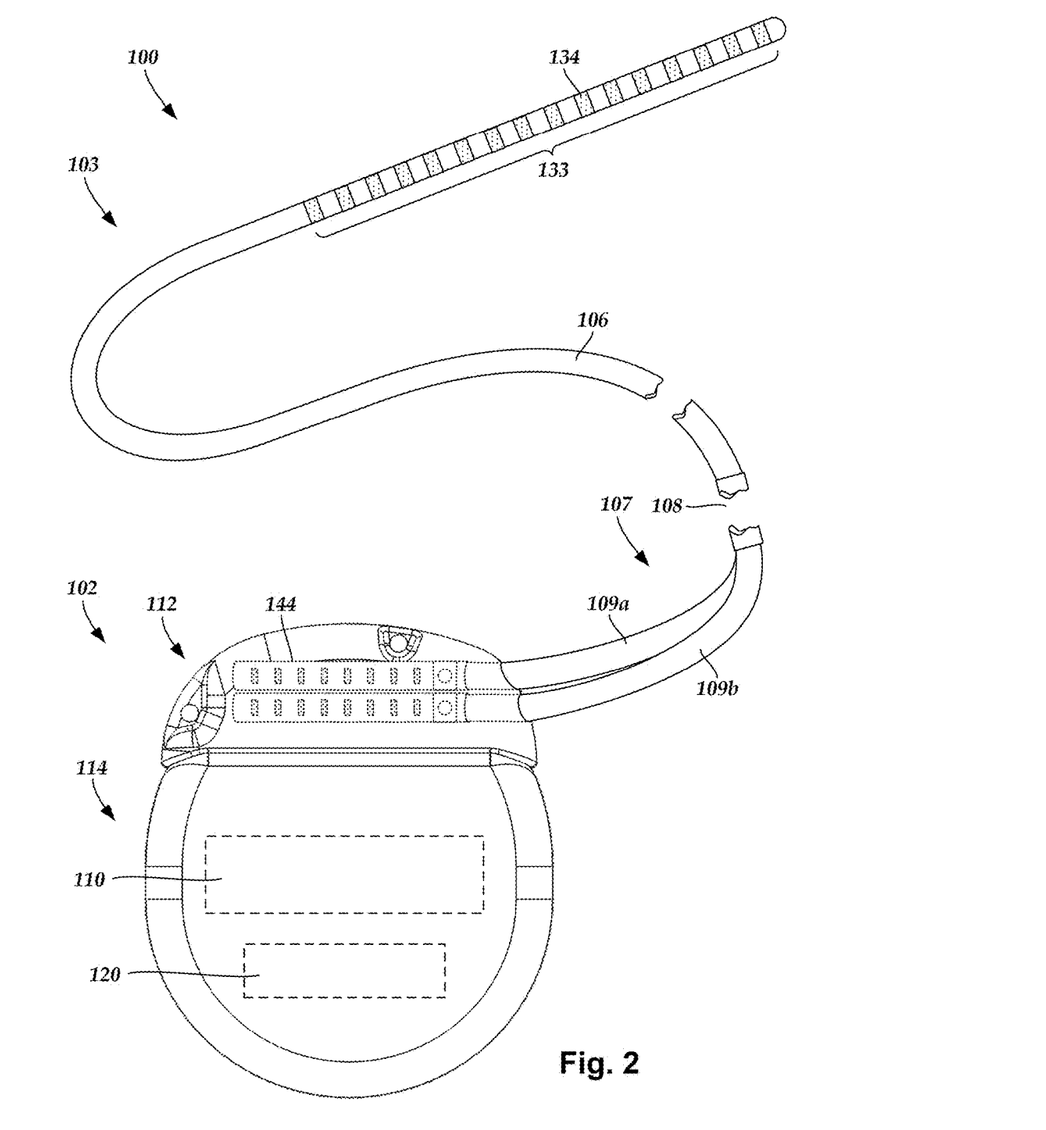
FIG. 2 is a schematic view of one embodiment of an electrical stimulation system that includes a percutaneous lead electrically coupled to a control module, according to the invention.

FIG. 2 illustrates schematically another embodiment of the electrical stimulation system 100, where the lead 103 is a percutaneous lead. In FIG. 2, the electrodes 134 are shown disposed along the one or more lead bodies 106. In at least some embodiments, the lead 103 is isodiametric along a longitudinal length of the lead body 106.

The lead 103 can be coupled to the control module 102 in any suitable manner. In FIG. 1, the lead 103 is shown coupling directly to the control module 102. In at least some other embodiments, the lead 103 couples to the control module 102 via one or more intermediate devices (324 in FIG. 3B). For example, in at least some embodiments one or more lead extensions 324 (see e.g., FIG. 3B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

In FIG. 2, the electrical stimulation system 100 is shown having a splitter 107 configured and arranged for facilitating coupling of the lead 103 to the control module 102. The splitter 107 includes a splitter connector 108 configured to couple to a proximal end of the lead 103, and one or more splitter tails 109a and 109b configured and arranged to couple to the control module 102 (or another splitter, a lead extension, an adaptor, or the like).

With reference to FIGS. 1 and 2, the control module 102 typically includes a connector housing 112 and a sealed electronics housing 114. An electronic subassembly 110 and an optional power source 120 are disposed in the electronics housing 114. A control module connector 144 is disposed in the connector housing 112. The control module connector 144 is configured and arranged to make an electrical connection between the lead 103 and the electronic subassembly 110 of the control module 102.

The electrical stimulation system or components of the electrical stimulation system, including the paddle body 104, the one or more of the lead bodies 106, and the control module 102, are typically implanted into the body of a patient. The electrical stimulation system can be used for a variety of applications including, but not limited to deep brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium.

Any suitable number of electrodes 134 can be disposed on the lead including, for example, four, five, six, seven, eight, nine, ten, eleven, twelve, fourteen, sixteen, twenty-four, thirty-two, or more electrodes 134. In the case of paddle leads, the electrodes 134 can be disposed on the paddle body 104 in any suitable arrangement. In FIG. 1, the electrodes 134 are arranged into two columns, where each column has eight electrodes 134.

The electrodes of the paddle body 104 (or one or more lead bodies 106) are typically disposed in, or separated by, a non-conductive, biocompatible material such as, for example, silicone, polyurethane, polyetheretherketone ("PEEK"), epoxy, and the like or combinations thereof. The one or more lead bodies 106 and, if applicable, the paddle body 104 may be formed in the desired shape by any process including, for example, molding (including injection molding), casting, and the like. The non-conductive material typically extends from the distal ends of the one or more lead bodies 106 to the proximal end of each of the one or more lead bodies 106.

In the case of paddle leads, the non-conductive material typically extends from the paddle body 104 to the proximal end of each of the one or more lead bodies 106. Additionally, the non-conductive, biocompatible material of the paddle body 104 and the one or more lead bodies 106 may be the same or different. Moreover, the paddle body 104 and the one or more lead bodies 106 may be a unitary structure or can be formed as two separate structures that are permanently or detachably coupled together.

Figure 3A:
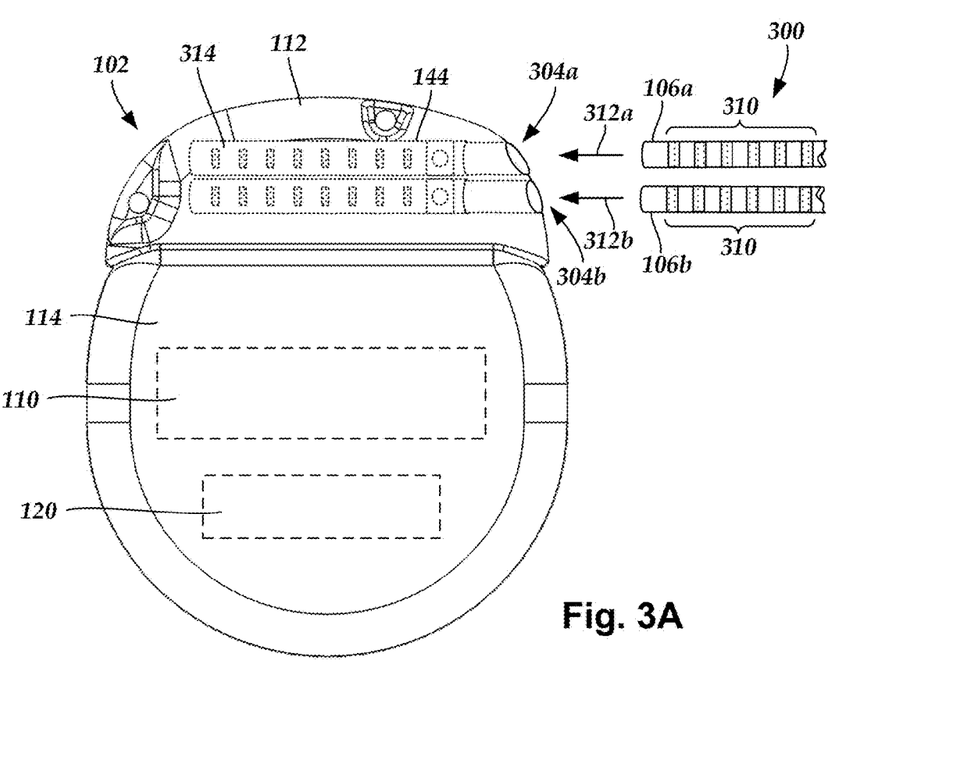
FIG. 3A is a schematic view of one embodiment of the control module of FIG. 1 configured and arranged to electrically couple to an elongated device, according to the invention.

Terminals (e.g., 310 in FIGS. 3A-3B) are typically disposed along the proximal end of the one or more lead bodies 106 of the electrical stimulation system 100 (as well as any splitters, lead extensions, adaptors, or the like) for electrical connection to corresponding connector contacts (e.g., 314 in FIG. 3A). The connector contacts are disposed in connectors (e.g., 144 in FIGS. 1-3B; and 322 FIG. 3B) which, in turn, are disposed on, for example, the control module 102 (or a lead extension, a splitter, an adaptor, or the like). Electrically conductive wires, cables, or the like (not shown) extend from the terminals to the electrodes 134. Typically, one or more electrodes 134 are electrically coupled to each terminal. In at least some embodiments, each terminal is only connected to one electrode 134.

The electrically conductive wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors extend through a lumen. There may also be one or more lumens (not shown) that open at, or near, the proximal end of the one or more lead bodies 106, for example, for inserting a stylet to facilitate placement of the one or more lead bodies 106 within a body of a patient. Additionally, there may be one or more lumens (not shown) that open at, or near, the distal end of the one or more lead bodies 106, for example, for infusion of drugs or medication into the site of implantation of the one or more lead bodies 106. In at least one embodiment, the one or more lumens are flushed continually, or on a regular basis, with saline, epidural fluid, or the like. In at least some embodiments, the one or more lumens are permanently or removably sealable at the distal end.

FIG. 3A is a schematic side view of one embodiment of a proximal end of one or more elongated devices 300 configured and arranged for coupling to one embodiment of the control module connector 144. The one or more elongated devices may include, for example, one or more of the lead bodies 106 of FIG. 1, one or more intermediate devices (e.g., a splitter, the lead extension 324 of FIG. 3B, an adaptor, or the like or combinations thereof), or a combination thereof.

The control module connector 144 defines at least one port into which a proximal end of the elongated device 300 can be inserted, as shown by directional arrows 312a and 312b. In FIG. 3A (and in other figures), the connector housing 112 is shown having two ports 305A and 305B. The connector housing 112 can define any suitable number of ports including, for example, one, two, three, four, five, six, seven, eight, or more ports.

The control module connector 144 also includes a plurality of connector contacts, such as connector contact 314, disposed within each port 305A and 305B. When the elongated device 300 is inserted into the ports 305A and 305B, the connector contacts 314 can be aligned with a plurality of terminals 310 disposed along the proximal end(s) of the elongated device(s) 300 to electrically couple the control module 102 to the electrodes (134 of FIG. 1) disposed on the paddle body 104 of the lead 103. Examples of connectors in control modules are found in, for example, U.S. Pat. Nos. 7,244,150 and 8,224,450, which are each incorporated by reference in their entirety.

Figure 3B:
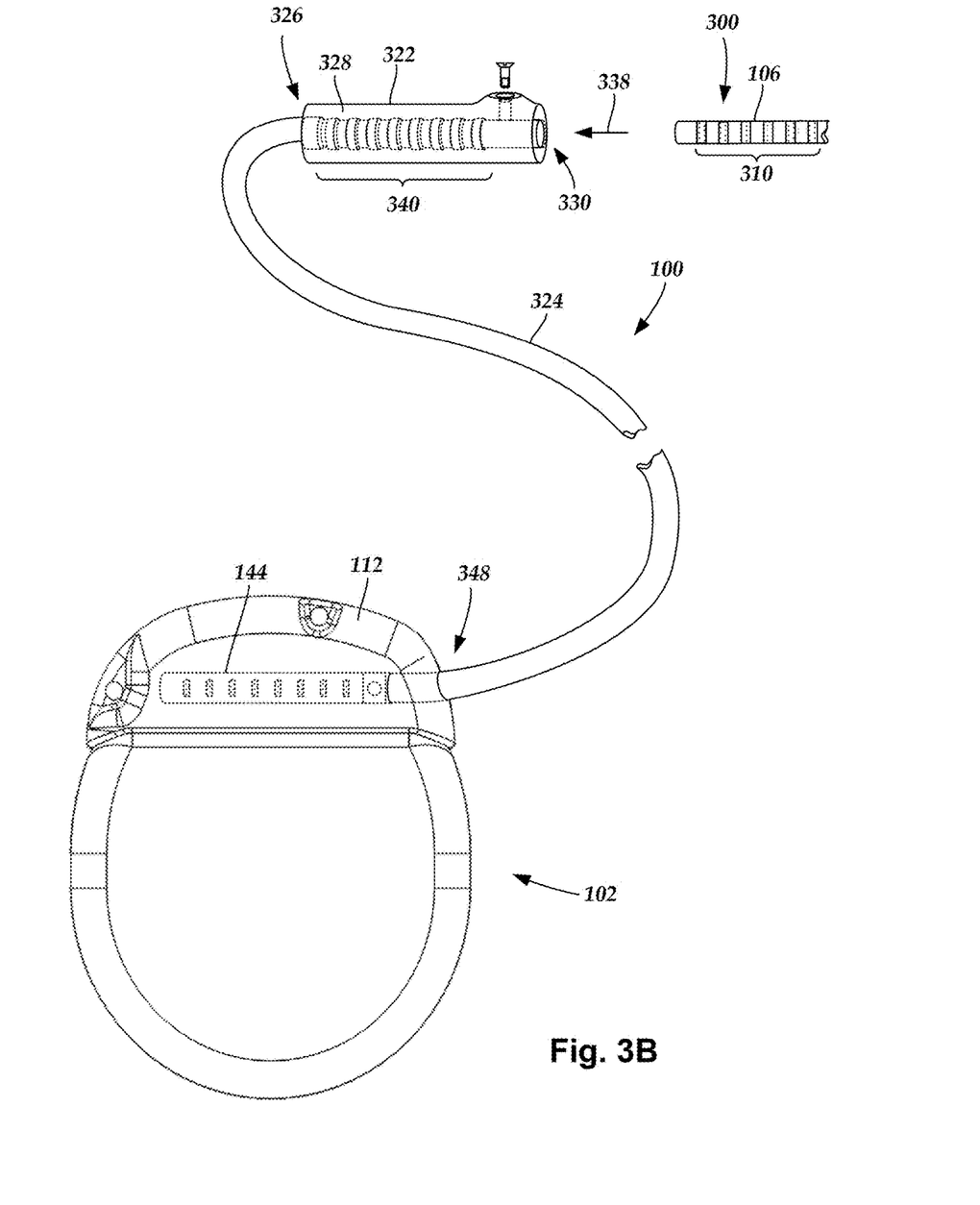
FIG. 3B is a schematic view of one embodiment of a lead extension configured and arranged to electrically couple the elongated device of FIG. 2 to the control module of FIG. 1, according to the invention.

FIG. 3B is a schematic side view of another embodiment of the electrical stimulation system 100. The electrical stimulation system 100 includes a lead extension 324 that is configured and arranged to couple one or more elongated devices 300 (e.g., one of the lead bodies 106 of FIGS. 1 and 2, the splitter 107 of FIG. 2, an adaptor, another lead extension, or the like or combinations thereof) to the control module 102. In FIG. 3B, the lead extension 324 is shown coupled to a single port 304 defined in the control module connector 144. Additionally, the lead extension 324 is shown configured and arranged to couple to a single elongated device 300. In alternate embodiments, the lead extension 324 is configured and arranged to couple to multiple ports 304 defined in the control module connector 144, or to receive multiple elongated devices 300, or both.

A lead extension connector 322 is disposed on the lead extension 324. In FIG. 3B, the lead extension connector 322 is shown disposed at a distal end 326 of the lead extension 324. The lead extension connector 322 includes a connector housing 328. The connector housing 328 defines at least one port 330 into which terminals 310 of the elongated device 300 can be inserted, as shown by directional arrow 338. The connector housing 328 also includes a plurality of connector contacts, such as connector contacts 340. When the elongated device 300 is inserted into the port 330, the connector contacts 340 disposed in the connector housing 328 can be aligned with the terminals 310 of the elongated device 300 to electrically couple the lead extension 324 to the electrodes (134 of FIGS. 1 and 2) disposed along the lead (103 in FIGS. 1 and 2).

In at least some embodiments, the proximal end of the lead extension 324 is similarly configured and arranged as a proximal end of the lead 103 (or other elongated device 300). The lead extension 324 may include a plurality of electrically conductive wires (not shown) that electrically couple the connector contacts 340 to a proximal end 348 of the lead extension 324 that is opposite to the distal end 326. In at least some embodiments, the conductive wires disposed in the lead extension 324 can be electrically coupled to a plurality of terminals (not shown) disposed along the proximal end 348 of the lead extension 324. In at least some embodiments, the proximal end 348 of the lead extension 324 is configured and arranged for insertion into a connector disposed in another lead extension (or another intermediate device). In other embodiments (and as shown in FIG. 3B), the proximal end 348 of the lead extension 324 is configured and arranged for insertion into the control module connector 144.

During testing of electrical stimulation for a patient, it is sometimes desirable to test the positioning or functionality of a lead within the patient to evaluate the results or efficacy of the electrical stimulation therapy. One way to test electrical stimulation therapy is to implant a distal end of a trial lead (and, optionally, one or more lead extensions) into the patient. The proximal end of the trial lead (or lead extension coupled to the trial lead) can then be electrically coupled to a trial stimulator that is disposed external to the patient to perform trial stimulations using the electrodes. Once it is determined that the electrodes are properly positioned and functioning within desired parameters, the trial stimulator and trial lead can be removed and replaced with a permanent lead attached to a control module.

The trial stimulations may continue for hours or days with the patient remaining in a hospital or other care facility. In other embodiments, the trial stimulations may continue for a short period (e.g., 7-10 days) where the patient is sent home with the trial lead, cable, and trial stimulator to assess the effectiveness of the therapy to determine if a permanent implanted system will be effective in treating the medical condition. During the trial stimulations, the trial lead can be electrically coupled to the trial stimulator by electrically coupling the proximal end of the trial lead (or lead extension coupled to the trial lead) to an operating room cable ("cable") that, in turn, is electrically coupled to the trial stimulator. In some cases, when multiple trial leads are implanted into a patient, multiple trial leads (or lead extensions) may be coupled to the cable.

Figure 4:
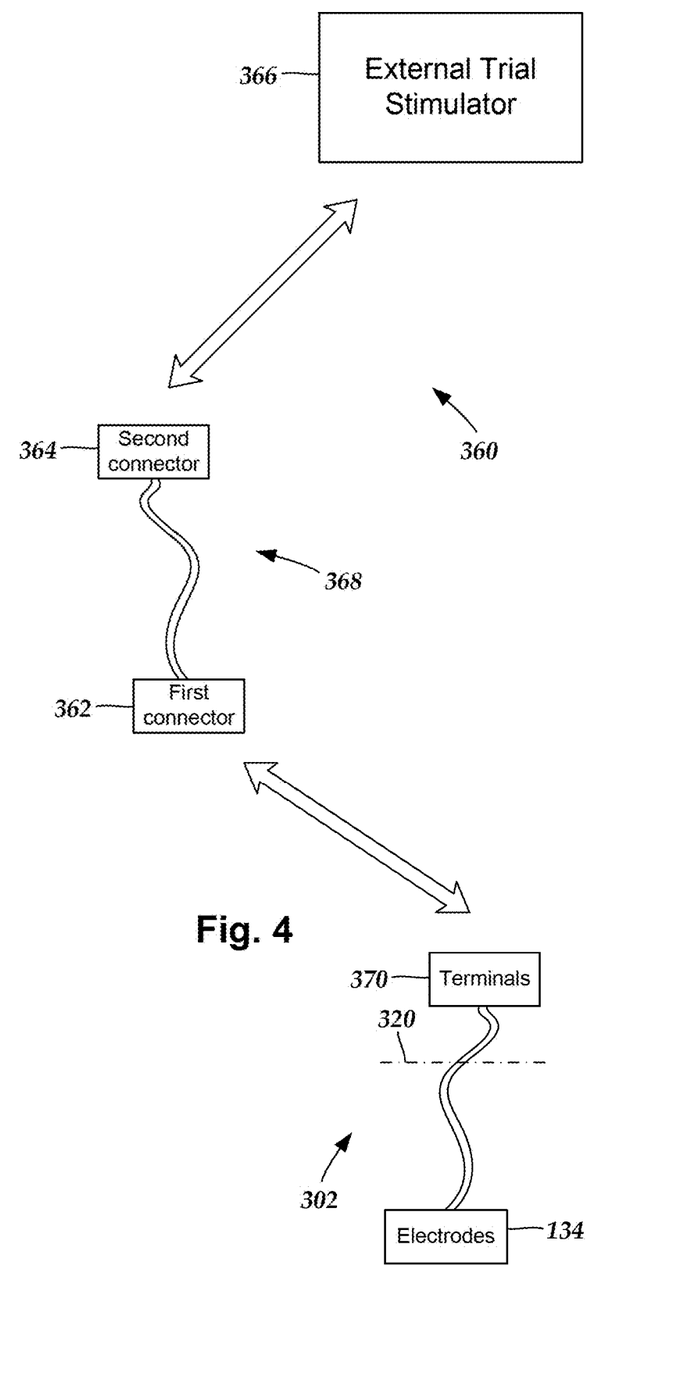
FIG. 4 is a schematic diagram of one embodiment of elements of an external trial stimulation system, according to the invention.

FIG. 4 is a schematic view of one embodiment of a trial stimulation arrangement 360 that includes a trial lead 302, an external trial stimulator 366, and one or more cables 368 that couple the trial lead 302 to the external trial stimulator 366. The trial lead 302 includes an array of electrodes 134 and an array of terminals 370. During operation, the electrodes 134 are disposed internal to the patient, while the terminals 370 remain external to the patient, as shown in FIG. 4 by a line 320 schematically representing patient skin. In at least some embodiments, the trial lead 302 is a percutaneous lead with a single proximal end. In alternate embodiments, the trial lead may be coupled to a lead extension, where the trial lead and a distal end of the lead extension are disposed in the patient while lead extension terminals remain external to the patient.

The terminals 370 are configured and arranged to couple the electrodes 134 to the external trial stimulator 366. In at least some embodiments, a lead connector 362 of the cable 368 is configured and arranged to couple to the terminals 370 of the trial lead 302 (or lead extension) and a trial stimulator connector 364 of the cable 368 is configured and arranged to couple to the external trial stimulator 366.

A variety of different cables can be used in a trial stimulation arrangement. Examples of such operating room cables can be found at, for example, U.S. Patent Applications Publication Nos. 2013/0098678 and 2015/0025609 and U.S. Provisional Patent Application Ser. No. 62/104,497; all of which are incorporated herein by reference in their entirety. Two examples of cables are described below for illustration purposes, but it will be understood that other cables can be used in a trial stimulation arrangement. It will also be understood that, although the description below is directed to coupling a lead to the cable, one of skill in the art will readily understand that a lead extension can be coupled to the cable with the lead extension attached to the implanted trial lead.

Figures 5A, 5B:
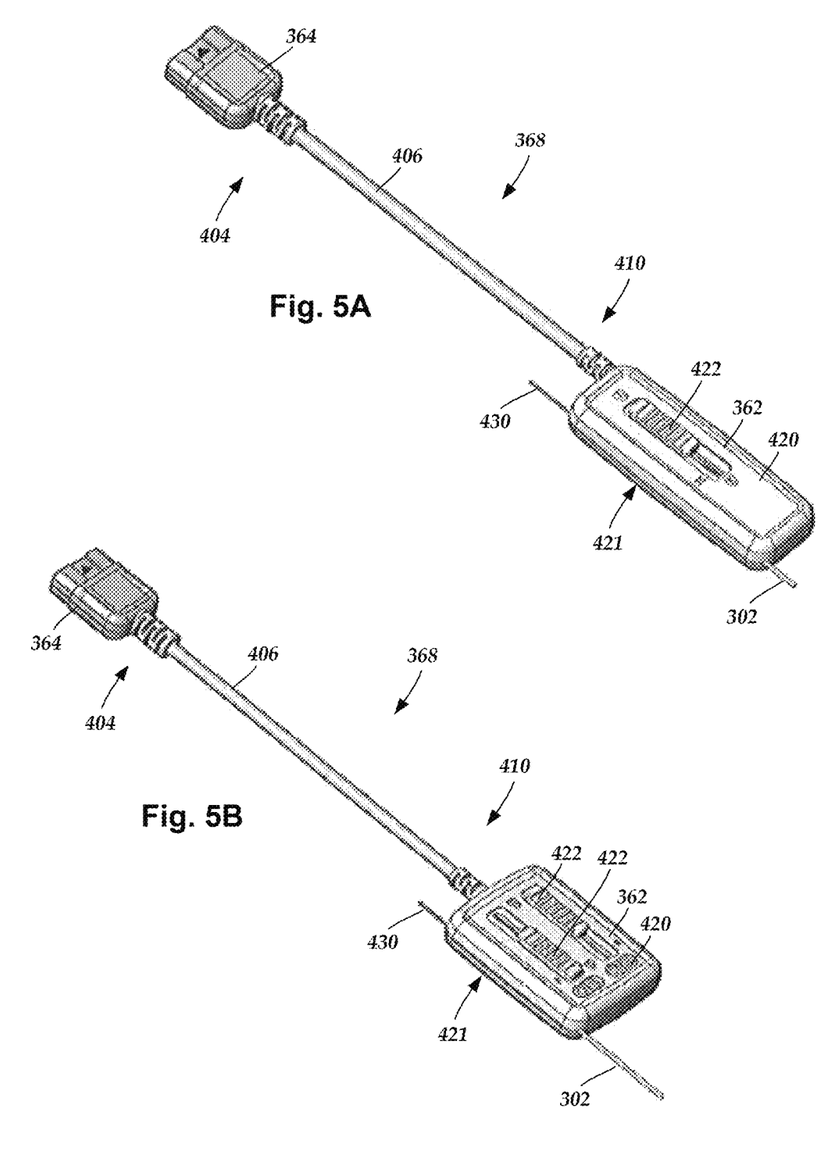
FIG. 5A is a schematic perspective view of one embodiment of an operating room cable, the operating room cable having a lead connector suitable for receiving a single lead, according to the invention.
FIG. 5B is a schematic perspective view of another embodiment of an operating room cable, the operating room cable having a lead connector suitable for receiving a plurality of leads, according to the invention.

FIGS. 5A and 5B illustrate two examples of cables 368 suitable for use in a trial stimulation arrangement 360. FIG. 5A is a schematic view of one embodiment of the cable 368 suitable for receiving a single trial lead 302. FIG. 5B is a schematic view of an alternate embodiment of the cable 368 suitable for receiving two trial leads 302. The cable 368 has an elongated body 406 with the trial stimulator connector 364 disposed at a first end 404 of the body 406, and the lead connector 362 disposed at a second end 410 of the body 406. The trial stimulator connector 364 is configured and arranged to couple to the external trial stimulator (366 in FIG. 4).

The lead connector 362 includes a housing 420 configured and arranged to receive the proximal end of the trial lead 302 and to electrically couple terminals of the trial leads to connector pins electrically coupled to the trial stimulator connector 364. The lead connector 362 can be configured and arranged to receive trial leads with any suitable number of terminals (370 in FIG. 4) including, for example, one, two, three, four, five, six, seven, eight, nine, ten, eleven, twelve, thirteen, fourteen, fifteen, sixteen, twenty, twenty-four, twenty-eight, thirty-two, or more terminals. It will be understood that received trial leads may include other numbers of terminals, as well.

In some cases, the lead connector 362 includes a mechanical locking feature 422 configured and arranged for locking the trial lead 302 within the housing 420 of the lead connector 362, thereby mechanically locking the trial lead 302 to the cable 368. As described in more detail below, when the trial lead 302 is locked within the housing 420, the terminals (370 in FIG. 4) electrically couple to connector pins (506 in FIG. 6A) disposed in the housing 420. Conversely, when the trial lead 302 is unlocked within the housing 420, the terminals (370 in FIG. 4) are electrically uncoupled from the connector pins (506 in FIG. 6A). The locking feature 422 can be any suitable tactile feature (e.g., a slidable button, or the like). Optionally, the housing 420 and the locking feature 422 are designed such that a medical practitioner can hold the housing 420 in one hand and operate the locking feature 422 to lock or unlock the trial lead 302 using the same hand (e.g., using his or her thumb or one or more other fingers) without the use of a mechanical tool.

Any suitable number of locking features 422 can be used to lock the trial lead(s) 302 within the housing 420. In preferred embodiments, a separate locking feature 422 is associated with each different trial lead 302 disposed in the housing 420. For example, in FIG. 5A a single locking element 422 is shown corresponding to a single received trial lead 302. In FIG. 5B, although the lead connector 362 is configured to receive two trial leads 302, only a single trial lead 302 is shown disposed in the housing 420 of the lead connector 362.

Figure 6A:
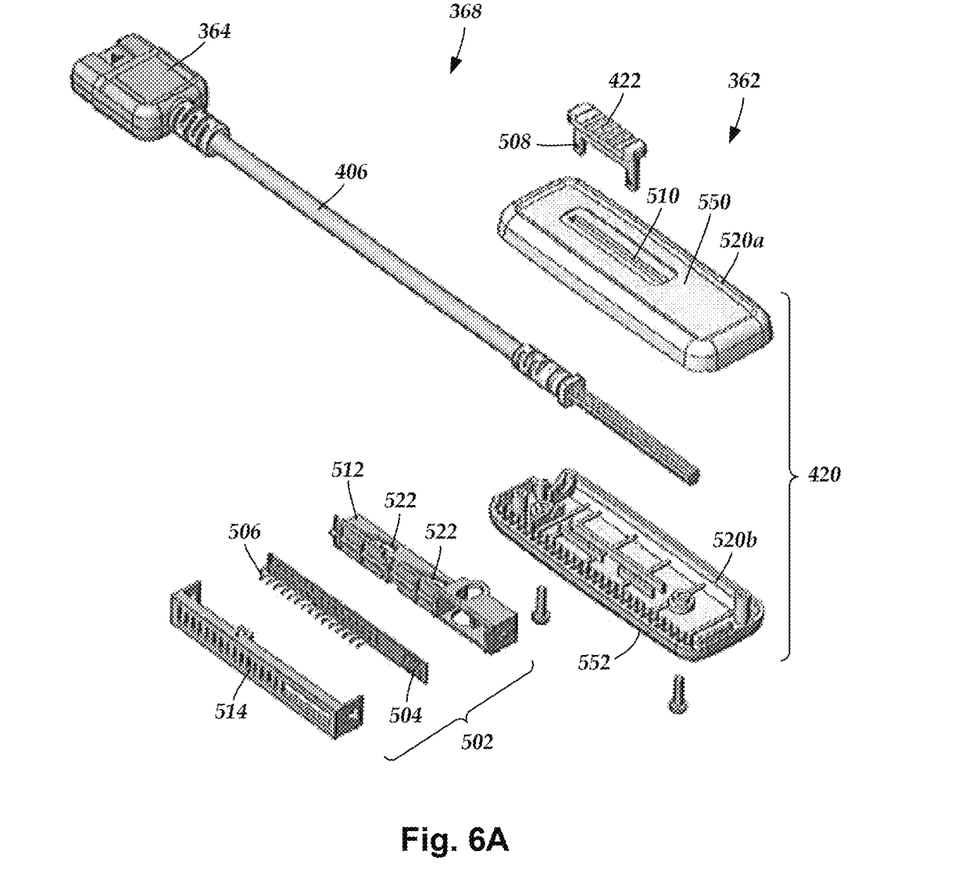
FIG. 6A is a schematic exploded, perspective view of the operating room cable of FIG. 5A, according to the invention.

FIG. 6A is a schematic exploded, perspective view of one embodiment of the lead connector 362 configured to receive a single trial lead 302. The lead connector 362 includes the housing 420. The housing 420 can be formed from any suitable material including, for example, plastic. In some cases, the housing 420 is formed from molded plastic. The housing 420 includes an upper casing 520a and a lower casing 520b. The upper casing 520a includes an upper major surface 550 and the lower casing 520b includes a lower major surface 552. The upper casing 520a and the lower casing 520b can be coupled together such that the upper major surface 550 and the lower major surface 552 oppose one another. The upper casing 520a and the lower casing 520b can be coupled together in any suitable manner including, for example, one or more screws, one or more snap-fit features, adhesive bonding, or the like.

A slide assembly 502, a printed circuit board 504 ("PCB"), and a plurality of connector pins 506 are each disposed within the housing 420. In at least some instances, the connector pins 506 are disposed directly on the PCB 504. The connector pins 506, in turn, are electrically coupled to conductors (not shown) that extend along a length of the body 406 and are electrically coupled to the trial stimulator connector 364.

The locking feature 422 is disposed external to the upper casing 520a and is coupled to one or more struts 508 that pass through a locking slit 510 in the upper casing 520a. In some instances, the one or more struts 508 are coupled to the upper casing 520a. For example, in at least some embodiments the locking feature 422 is coupled to the upper casing 520a by one or more interference bumps that are molded into the sides of the one or more struts 508 and that snap-fit thru the slot 510. The one or more struts 508 couple the locking feature 422 to the slide assembly 502 such that movement of the locking feature 422 causes a corresponding movement of the slide assembly 502.

The slide assembly 502 includes a slide 512 and a slide frame 514. The slide 512 defines one or more curved slots 522 through which the one or more struts 508 extend. The PCB 504 is disposed within the slide assembly 502 such that movement of the slide assembly 502 causes a corresponding movement of the PCB 504 which, in turn, causes a corresponding lateral movement of the connector pins 506. In at least some embodiments, the PCB 504 is locked within the slide assembly 502. In at least some embodiments, the PCB 504 is bonded or snap-fit directly to the slide 512. In which case, the slide frame 514 may be omitted.

As described above, the slide 512 defines one or more curved slots 522 through which the one or more struts 508 extend. In at least some embodiments, when a user moves the locking feature 422 along the locking slit 510 in the upper casing 520a, the one or more struts 508 move along the curved slots 522. The curvature of the curved slots 522 causes lateral movement of the slide assembly 502 relative to the movement of the locking feature 522.

When the trial lead 302 is disposed in the lead connector 362, the lateral movement of the slide assembly 502 relative to the locking feature 422 causes the connector pins 506 to electrically couple or uncouple with the terminals 370 of the trial lead 302. In at least some embodiments, the movement of the locking feature 422 along the locking slit 510 is perpendicular to the movement of the connector pins 506. In at least some embodiments, the connector pins 506 move away from the locking feature 422 to electrically couple with the lead terminals (i.e., transition to a locked position), and towards the locking feature 422 to electrically uncouple from the lead terminals (i.e., transition to an unlocked position).

Figure 6B:
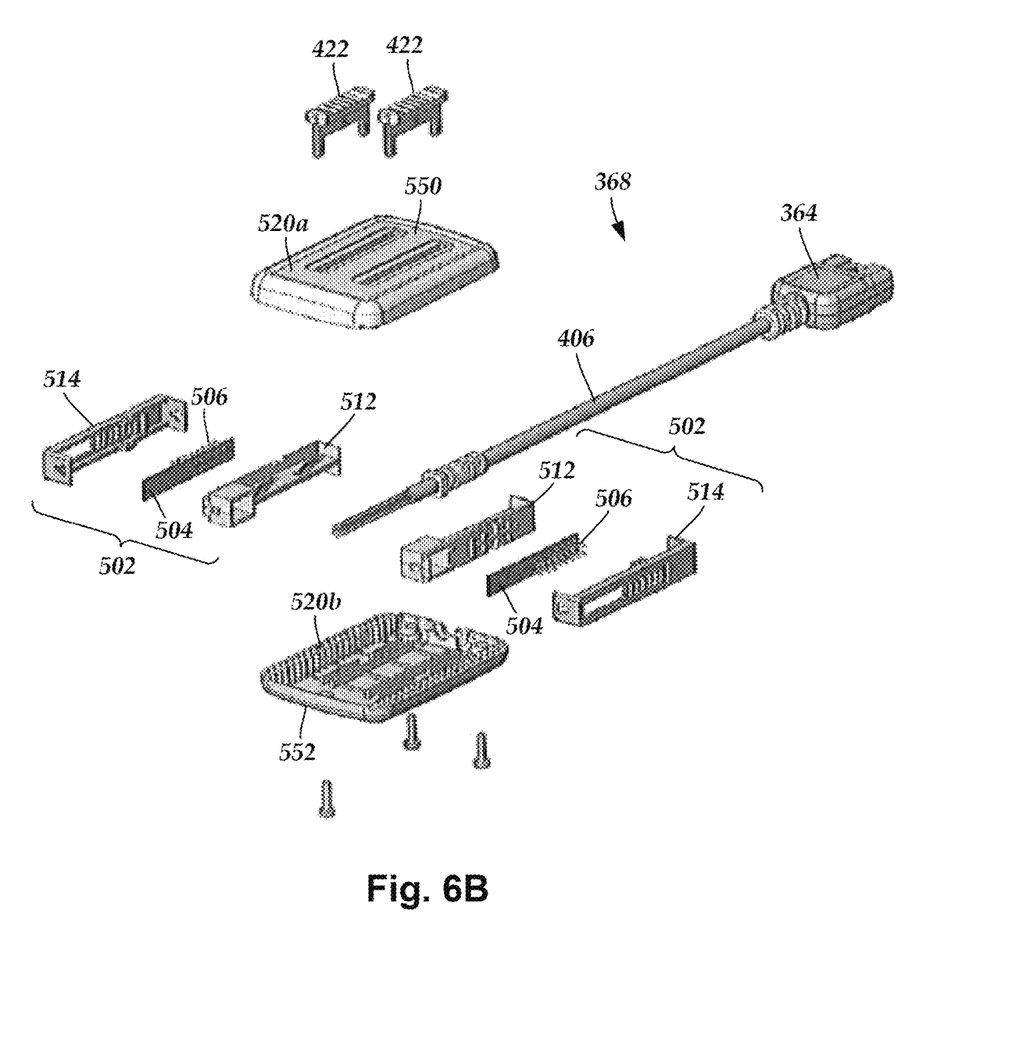
FIG. 6B is a schematic exploded, perspective view of the operating room cable of FIG. 5B, according to the invention.

FIG. 6B is a schematic exploded, perspective view of one embodiment of the lead connector 362 configured to receive a plurality of trial leads 302. In FIG. 6B, the lead connector 362 is configured to receive two trial leads 302. The components of the multi-lead-receiving lead connector 362 of FIG. 6B are similar to the components of the single-lead-receiving lead connector 362, described above with reference to FIG. 6A. The multi-lead-receiving lead connector 362 shown in FIG. 6B, however, includes a separate locking feature 422, slide assembly 502, PCB 504 and plurality of connector pins 506 for each trial lead 302 that the lead connector 362 is configured to receive. For example, in FIG. 6B, the lead connector 362 includes two locking features 422, two slide assemblies 502, two PCB 504, and two pluralities of connector pins 506.

In each of the embodiments of the lead connector 362 described above, with reference to FIGS. 6A-6B, the lead connectors 362 are configured to receive the trial lead(s) with stylets that are inserted into the trial leads and that engage the lead connectors from one or more sides of the lead connector (e.g., a side-loading lead connector). In the case of the embodiment of the multi-lead-receiving embodiment of the lead connector 362, the stylets are received on opposing sides of the lead connector 362.

A stiffening member, such as a stylet 430, is sometimes used to adjust the positioning of a distal end of the trial lead 302 to a desired position within the patient. The stylet 430 is sometimes inserted into the trial lead 302 through a proximal end of the trial lead 302 such that a portion of the stylet 430 extends from the proximal end of the trial lead 302. The exposed portion of the stylet 430 may be used to adjust the positioning of the trial lead 302. It is sometimes desirable to retain the stylet 430 within the trial lead 302 during trial stimulation in order to facilitate further adjustment of the positioning of the trial lead 302 during, or subsequent to, the trial stimulation.

Stylets typically have a cap, or handle, that facilitates gripping of the stylet 430 during adjustment of the positioning of the trial lead 302. Conventional stylet handles have diameters that are larger than other portions of the stylet and trial lead and may hinder, or even prevent, a trial lead from coupling with a cable without first removing the stylet from the trial lead. As herein described, the lead connector 362 is configured and arranged to receive the trial lead 302 such that, when the stylet 430 is disposed in the trial lead 302, the stylet 430 is available for use to guide the trial lead 302 while the trial lead 302 is locked within the housing 420. In at least some embodiments, when the proximal end of the trial lead 302 is disposed in the housing 420, the trial lead 302 and the stylet 430 each extend from opposing ends of the housing 420.

In some embodiments, the lead connector 362 has a side slit 421 (FIGS. 5A and 5B). In at least some embodiments, the side slit 421 has a width that is sufficient for the stylet 430 to pass through the side slit (i.e., the width of the side slit is greater than the diameter of the stylet), but will not allow the trial lead 302 to pass through the side slit (i.e., the width of the side slit is less than the diameter of the trial lead.)

In some embodiments, the trial lead is intended to be compatible with the cable to allow for testing, but is not compatible for long-term implantation. For example, the trial lead may have fewer electrodes, lack anchoring or other features, or lack MRI compatibility or the like. It is useful to have a trial lead that can be used with a cable of an external trial stimulation system, but which cannot be used with an implantable control module. Such an arrangement will remind the practitioner that the trial lead is only for use with an external trial stimulation system and should be replaced with a suitable implantable lead for use with the implantable control module.

Figure 7A:
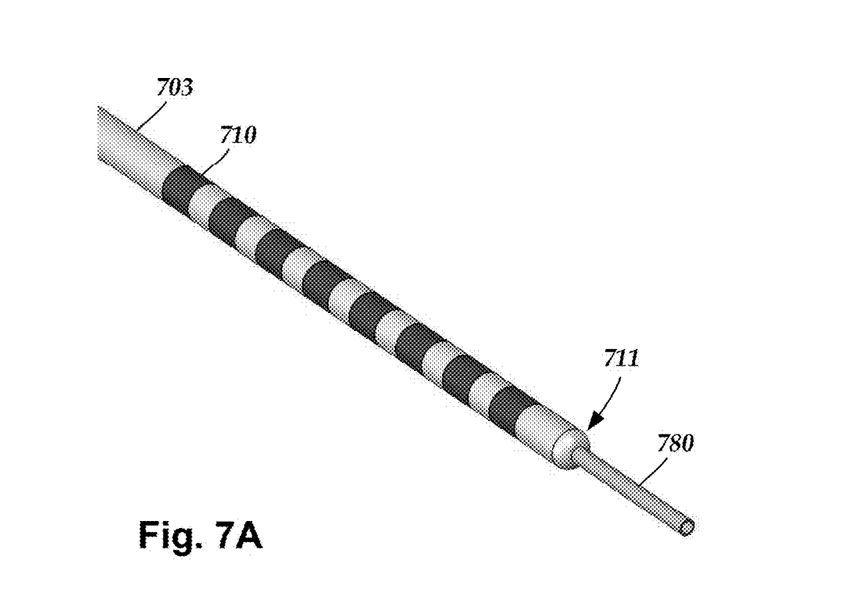
FIG. 7A is a schematic perspective view of a proximal end of one embodiment of a trial lead with a preventer, according to the invention.
Figure 7B:
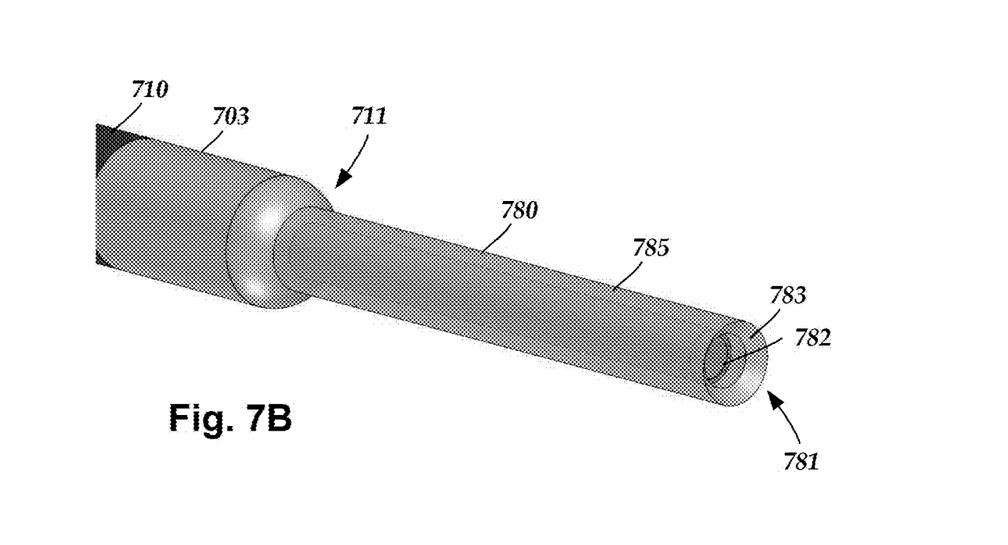
FIG. 7B is a schematic perspective view of a proximal end of another embodiment of a trial lead with a preventer, according to the invention.

FIGS. 7A and 7B illustrate a proximal end of a trial lead 703 with terminals 710. Extending from the proximal tip 711 of the trial lead 703 is a preventer 780 arranged to prevent the trial lead from properly coupling with an implantable control module. In at least some embodiments, the preventer 780 has a smaller diameter than the lead body of the trial lead 703. In at least some embodiments, the preventer 780 is partially disposed within the central lumen the trial lead 703 and is adhesively or otherwise attached to the trial lead 703. In at least some embodiments, the preventer 780 is permanently attached to the trial lead 703 so that a user cannot remove the preventer without damaging the trial lead. In at least some embodiments, the preventer 780 extends along a part of the central lumen of the trial lead 703. The preventer 780 may along the central lumen so that it is radially beneath one or more (or a majority of or all of) the terminals 710 of the trial lead 703. Such an arrangement can stiffen the proximal end of the trial lead 703 to facilitate coupling to a connector.

In at least some embodiments, the preventer 780 can be, for example, a tubular element 782, such as a hypotube. In at least some embodiments, the preventer 780 includes a lumen 781 (FIG. 7B) that extends to the central lumen of the trial lead 703.

In at least some instances, a stylet (such as stylet 430 of FIG. 5A or 5B) can be inserted into the trial lead 703 through the lumen 781 of the preventer 780. In at least some embodiments, the proximal tip of the preventer 780 can be flared, beveled, or have a radiused edge 783, as illustrated in FIG. 7B, to facilitate insertion of the stylet into the lumen 781. In other embodiments, the preventer 780 can be a solid tube. In some embodiments, the preventer 780 may include a polymer jacket 785 (FIG. 7B) disposed around the tubular element 782 to soften the outer surface of the preventer to avoid tearing a surgical glove or causing other damage. The polymer jacket 785 may have a proximal tip that forms the flared, beveled, or radiused edge 783.

The preventer 780, when inserted into a control module (such as control module 102 of FIG. 1), will engage the end of a connector port of the control module and prevent correct coupling of the trial lead to the implantable control module. For example, the preventer 780 can prevent one or more of (or, preferably, all of) the terminals 710 of the trial lead 703 from contact with the contacts in the connector (for example, connector 144 of FIG. 1) of the control module. Thus, the preventer 780 prevents proper coupling of the trial lead with an implantable control module.

In at least some embodiments, the preventer 780, when inserted into a connector of a lead extension (for example, lead extension 324 of FIG. 3B), will prevent one or more of (or, preferably, all of) the terminals 710 of the trial lead 703 from contact with the contacts in the connector of the lead extension. Thus, the preventer 780 prevents proper coupling of the trial lead with a lead extension.

The preventer 780 is attached to the trial lead 703 to provide a visual reminder that the lead 703 is a trial lead and not for long-term implantation. The preventer 780 can also provide a tactile reminder, when inserted into a connector of a control module or lead extension, that the lead 703 is a trial lead and not for long-term implantation.

In contrast, when the trial lead 703 is inserted into the connector of a cable of an external trial stimulation system (such as lead connector 362 of FIGS. 5A-6B) which is designed to accommodate a stylet within the lead, the preventer 780 does not prevent contact between the terminals 710 of the trial lead and the contacts within the connector of the cable. For example, when a lead is inserted into a connector of a cable, the preventer 780 can be extend outside the connector similar to the stylet 430 extending outside the lead connector 362 in FIGS. 5A and 5B.

Referring to lead connectors 362 in FIGS. 5A-6B as illustrative examples of a lead connector of a cable, in at least some embodiments, the preventer 780 can be inserted into the lead connector 362 from the same end as the proximal end of the lead 703. In at least some embodiments, for a lead connector (e.g., lead connector 362 of FIG. 5A or 5B) having a side slit 421, the preventer can be inserted through a side slit that has a width greater than the diameter of the preventer 780, but will not allow the trial lead 703 to pass through the side slit (i.e., the width of the side slit is less than the diameter of the trial lead.)

Figure 8:
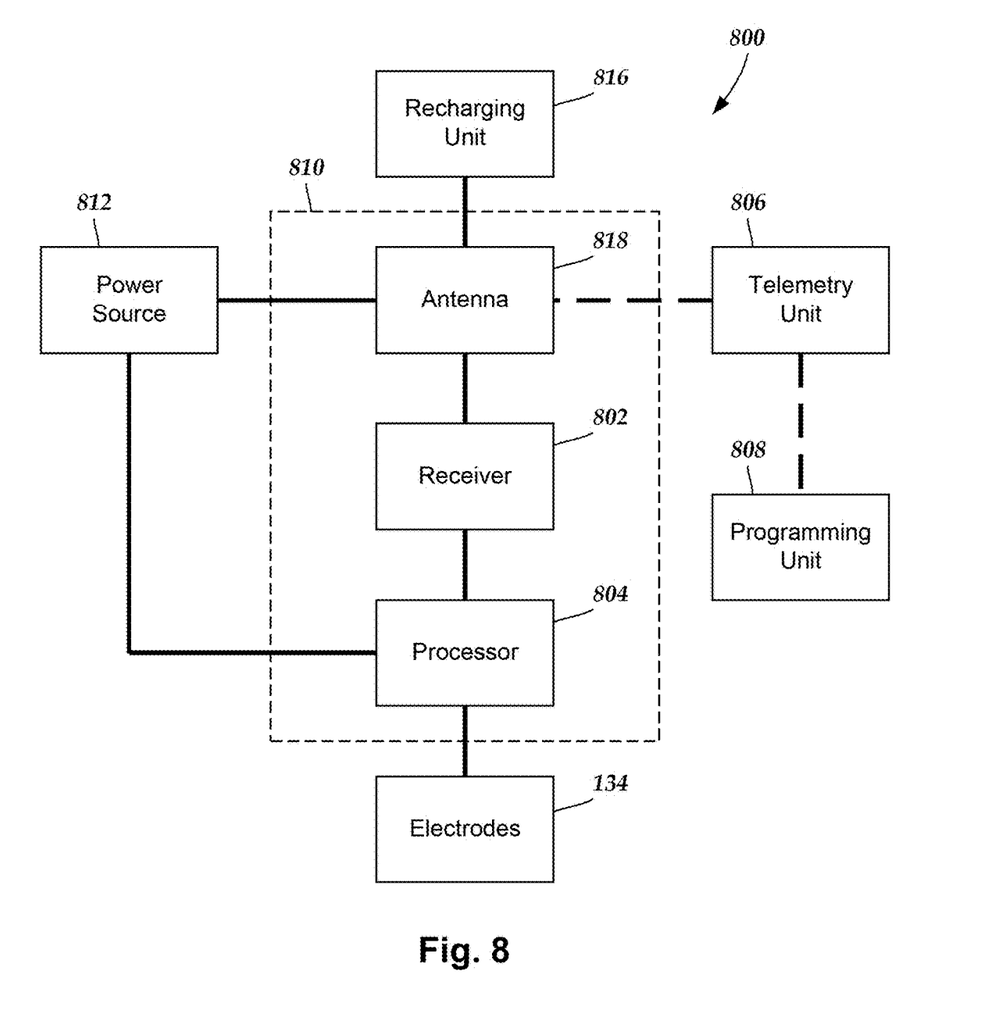
FIG. 8 is a schematic overview of one embodiment of components of a stimulation system, including an electronic subassembly disposed within a control module, according to the invention.

FIG. 8 is a schematic overview of one embodiment of components of an electrical stimulation system 800 including an electronic subassembly 810 disposed within a control module. It will be understood that the electrical stimulation system can include more, fewer, or different components and can have a variety of different configurations including those configurations disclosed in the stimulator references cited herein.

Some of the components (for example, power source 812, antenna 818, receiver 802, and processor 804) of the electrical stimulation system can be positioned on one or more circuit boards or similar carriers within a sealed housing of an implantable pulse generator, if desired. Any power source 812 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference in its entirety.

As another alternative, power can be supplied by an external power source through inductive coupling via the optional antenna 818 or a secondary antenna. The external power source can be in a device that is mounted on the skin of the user or in a unit that is provided near the user on a permanent or periodic basis.

If the power source 812 is a rechargeable battery, the battery may be recharged using the optional antenna 818, if desired. Power can be provided to the battery for recharging by inductively coupling the battery through the antenna to a recharging unit 816 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 804 is generally included to control the timing and electrical characteristics of the electrical stimulation system. For example, the processor 804 can, if desired, control one or more of the timing, frequency, strength, duration, and waveform of the pulses. In addition, the processor 804 can select which electrodes can be used to provide stimulation, if desired. In some embodiments, the processor 804 may select which electrode(s) are cathodes and which electrode(s) are anodes. In some embodiments, the processor 804 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 808 that, for example, allows modification of pulse characteristics. In the illustrated embodiment, the processor 804 is coupled to a receiver 802 which, in turn, is coupled to the optional antenna 818. This allows the processor 804 to receive instructions from an external source to, for example, direct the pulse characteristics and the selection of electrodes, if desired.

In one embodiment, the antenna 818 is capable of receiving signals (e.g., RF signals) from an external telemetry unit 806 which is programmed by a programming unit 808. The programming unit 808 can be external to, or part of, the telemetry unit 806. The telemetry unit 806 can be a device that is worn on the skin of the user or can be carried by the user and can have a form similar to a pager, cellular phone, or remote control, if desired. As another alternative, the telemetry unit 806 may not be worn or carried by the user but may only be available at a home station or at a clinician's office.

The programming unit 808 can be any unit that can provide information to the telemetry unit 806 for transmission to the electrical stimulation system 800. The programming unit 808 can be part of the telemetry unit 806 or can provide signals or information to the telemetry unit 806 via a wireless or wired connection. One example of a suitable programming unit is a computer operated by the user or clinician to send signals to the telemetry unit 806.

The signals sent to the processor 804 via the antenna 818 and receiver 802 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 800 to cease operation, to start operation, to start charging the battery, or to stop charging the battery. In other embodiments, the stimulation system does not include an antenna 818 or receiver 802 and the processor 804 operates as programmed.

Optionally, the electrical stimulation system 800 may include a transmitter (not shown) coupled to the processor 804 and the antenna 818 for transmitting signals back to the telemetry unit 806 or another unit capable of receiving the signals. For example, the electrical stimulation system 800 may transmit signals indicating whether the electrical stimulation system 800 is operating properly or not or indicating when the battery needs to be charged or the level of charge remaining in the battery. The processor 804 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. An electrical stimulation lead, comprising:
   a lead body having a distal end portion, a proximal end portion, and a longitudinal length;
   a plurality of electrodes disposed along the distal end portion of the lead body;
   a plurality of terminals disposed along the proximal end portion of the lead body;
   a plurality of conductors electrically coupling the plurality of terminals to the plurality of electrodes; and
   a preventer permanently extending proximally from the proximal end portion of the lead body, wherein the preventer has a diameter smaller than a diameter of the lead body and has a polymer jacket forming an entire outer surface of the preventer.

2. The electrical stimulation lead of claim 1, wherein the lead body defines a central lumen extending from the proximal end portion to the distal end portion, wherein a portion of the preventer is disposed within the central lumen.

3. The electrical stimulation lead of claim 2, wherein the preventer further comprises a tube defining a lumen extending along the tube, wherein the lumen defines an inner surface of the preventer.

4. The electrical stimulation lead of claim 3, wherein the lumen of the preventer is in communication with the central lumen of the lead body.

5. The electrical stimulation lead of claim 4, further comprising a stylet configured and arranged for insertion through the lumen of the preventer into the central lumen of the lead body.

6. The electrical stimulation lead of claim 3, wherein the polymer jacket is disposed over the tube of the preventer to soften the outer surface of the preventer.

7. The electrical stimulation lead of claim 6, wherein the polymer jacket comprises a proximal tip that is flared, beveled, or has a radiused inside edge.

8. The electrical stimulation lead of claim 2, wherein the preventer comprises a proximal tip that is flared, beveled, or has a radiused inside edge to facilitate insertion of a stylet into the lumen of the preventer.

9. The electrical stimulation lead of claim 2, wherein the portion of the preventer disposed within the central lumen is disposed radially beneath at least one of the terminals.

10. The electrical stimulation lead of claim 2, wherein the portion of the preventer disposed within the central lumen is disposed radially beneath all of the terminals.

11. A method of using the electrical stimulation lead of claim 1, the method comprising:
    inserting the electrical stimulation lead into a patient; and
    coupling the electrical stimulation lead to a cable of an external trial stimulation system.

12. The method of claim 11, further comprising
    removing the electrical stimulation lead;
    implanting a permanent electrical stimulation lead into the patient; and
    coupling the permanent electrical stimulation lead to an implantable control module.

13. An electrical stimulation system, comprising:
    the electrical stimulation lead of claim 1; and
    an operating room cable for electrically coupling the electrical stimulation lead to a trial stimulator, the operating room cable comprising:
       an elongated body having a first end and an opposing second end;

a trial stimulator connector disposed at the first end of the body, and electrically coupleable with the trial stimulator; and a lead connector disposed at the second end of the body and electrically coupled to the trial stimulator connector, the lead connector configured and arranged to mechanically receive the proximal end portion of the lead body of the electrical stimulation lead.

14. The electrical stimulation system of claim 13, wherein the lead connector comprises a housing, a first lead aperture in the housing for receiving the proximal end portion of the lead body, and a side slit defined along the housing, parallel the first lead aperture, and in communication with the first lead aperture.

15. The electrical stimulation system of claim 14, wherein a width of the side slit is less than a diameter of the lead body of the electrical stimulation lead.

16. The electrical stimulation system of claim 15, wherein the width of the side slit is more than a diameter of the preventer of the electrical stimulation lead.

* * * * *